US008865201B2

(12) United States Patent
De Luigi Bruschi et al.

(10) Patent No.: US 8,865,201 B2
(45) Date of Patent: Oct. 21, 2014

(54) USE OF A HYDROPHILIC MATRIX COMPRISING A POLYACRYLIC ACID DERIVATIVE, A CELLULOSE ETHER AND A DISINTEGRANT IN THE MANUFACTURE OF A MEDICAMENT FOR TREATING FEMALE GENITAL DISORDERS

(75) Inventors: Stefano De Luigi Bruschi, Milan (IT); Federico Mailland, Lugano (CH)

(73) Assignee: Polichem SA, Luxembourg (LU)

( * ) Notice: Subject to any disclaimer, the term of this patent is extended or adjusted under 35 U.S.C. 154(b) by 630 days.

(21) Appl. No.: 12/308,786

(22) PCT Filed: Jun. 21, 2007

(86) PCT No.: PCT/EP2007/056185
§ 371 (c)(1),
(2), (4) Date: Jun. 1, 2009

(87) PCT Pub. No.: WO2008/000683
PCT Pub. Date: Jan. 3, 2008

(65) Prior Publication Data
US 2011/0091555 A1     Apr. 21, 2011

(30) Foreign Application Priority Data

Jun. 29, 2006  (EP) .................... 06116269

(51) Int. Cl.
| A61K 9/00 | (2006.01) |
| A61K 9/20 | (2006.01) |
| A61K 9/52 | (2006.01) |
| A61K 31/4418 | (2006.01) |
| A61P 15/02 | (2006.01) |
| A61P 31/00 | (2006.01) |
| A61K 31/496 | (2006.01) |

(52) U.S. Cl.
CPC ............ *A61K 31/496* (2013.01); *A61K 9/0039* (2013.01); *A61K 9/2054* (2013.01)
USPC ........... 424/430; 424/433; 424/464; 424/468; 424/480; 424/487

(58) Field of Classification Search
CPC .. A61K 31/496; A61K 9/0039; A61K 9/2054
USPC .................. 424/430, 433, 464, 468, 480, 487
See application file for complete search history.

(56) References Cited

U.S. PATENT DOCUMENTS

| 2,096,744 | A | 10/1937 | Hildebrandt et al. |
| 2,232,438 | A | 2/1941 | Butenandt |
| 2,243,887 | A | 6/1941 | Serini et al. |
| 2,251,939 | A | 8/1941 | Kathol |
| 2,265,976 | A | 12/1941 | Inhoffen et al. |
| 2,267,257 | A | 12/1941 | Ruzicka |
| 2,314,185 | A | 3/1943 | Zondek et al. |
| 2,379,832 | A | 7/1945 | Serini et al. |
| 3,340,279 | A | 9/1967 | De Jongh et al. |
| 3,475,465 | A | 10/1969 | De Winter et al. |
| 4,292,299 | A * | 9/1981 | Suzuki et al. ............. 424/435 |
| 6,416,779 | B1 | 7/2002 | D. Augustine et al. |
| 2003/0059456 | A1 * | 3/2003 | Malcolm et al. ............ 424/430 |
| 2003/0180366 | A1 * | 9/2003 | Kirschner et al. ............ 424/489 |

FOREIGN PATENT DOCUMENTS

| CN | 1679511 | 10/2005 |
| GB | 516444 | 1/1940 |
| JP | 2004500317 | 1/2004 |
| JP | 2004501190 | 1/2004 |
| JP | 2004509142 | 3/2004 |
| WO | WO0010536 | 3/2000 |
| WO | WO 01/24788 A2 | 4/2001 |
| WO | 02/03896 | 1/2002 |
| WO | WO0200213 | 1/2002 |
| WO | WO0220170 | 3/2002 |
| WO | 2006/017238 | 2/2006 |

OTHER PUBLICATIONS

Zhao, et al., AAPS PharmSciTech, 2005, 6, E634-E640.
Cao, et al., J. Control Release, 2005, 108, 351-361 (Abstract).

* cited by examiner

*Primary Examiner* — Mina Haghighatian
(74) *Attorney, Agent, or Firm* — Hueschen and Sage (57) ABSTRACT

A hydrophilic matrix is disclosed which comprises:
a) at least one polyacrylic acid derivative in preferred amounts of 0.5-40%,
b) at least one cellulose ether in preferred amounts of 30-90% and
c) at least one disintegrant in preferred amounts of 2-50%, with respect to the weight of the matrix.
This matrix is used in combination with at least one pharmaceutically acceptable active principle for manufacturing solid bioadhesive controlled release formulations for the treatment of vaginal disorders, such as vulvovaginal candidiasis, bacterial vaginosis or trichomoniasis.
According to a preferred embodiment, the matrix is used in amounts of about 5-60% and the active principle in amounts of about 2-70%, with respect to the weight of the formulation.

17 Claims, 2 Drawing Sheets

USE OF A HYDROPHILIC MATRIX COMPRISING A POLYACRYLIC ACID DERIVATIVE, A CELLULOSE ETHER AND A DISINTEGRANT IN THE MANUFACTURE OF A MEDICAMENT FOR TREATING FEMALE GENITAL DISORDERS

The present invention relates to bioadhesive controlled release tablets for vaginal drug delivery to be used for the treatment of female genital disorders.

Vaginal delivery is an important route of drug administration for both local and systemic diseases. However this route of administration even though has a lot of advantages such as self insertion and avoidance of the first-pass effect, has not been extensively exploited because of the broad inter-individual variability affecting some physiological factors like the pH and the presence of limited vaginal secretions that further vary depending on age and menstrual cycles.

Moreover, commercial presentations such as creams, foams, gels, irrigations, tablets are considered to reside in the vaginal cavity for a relatively short period of time by the self-cleaning action of the vaginal tract and often require multiple daily dose to ensure the desired therapeutic effect.

To prolong the residence time in the vaginal cavity, bioadhesive therapeutic systems have been developed in the form of semi-solid and solid dosage forms.

Bioadhesive semi-solid presentations such as creams, foams, gels have the advantage to promote the release of the drug in the vaginal cavity even in absence of physiological secretions.

This is due because the drug is finely dispersed or dissolved in the liquid vehicle (aqueous or oily phases or mixtures thereof) constituting the dosage form. Such a highly drug dispersion in the semisolid dosage forms, associated with a low concentration, is in turn responsible of a lower incidence of local irritation phenomena of the mucosa thanks to the its spreading on a high surface of the vaginal epithelium. As a result, a good patient compliance is usually met.

However these systems are not generally designed to ensure any efficient release control of the drug which is entirely available for immediate release in the vaginal cavity.

Conversely, aqueous based systems cannot be used with water sensitive drugs, oil based systems show a lower patient compliance and oil in water or water in oil emulsions often suffer a poor physical stability leading to separation phenomena.

Last but not least, these systems have also the disadvantage of requiring the use of applicators to be introduced in the vaginal cavity.

Bioadhesive solid dosage forms such as tablets, lozenges, suppositories (vaginal inserts), are known for their ease of administration associated with reduced stability problems in comparison with semi-solid presentations.

On the contrary they show a poor drug diffusion pattern because of the limited quantities of physiological fluids in the vaginal cavity. They are responsible also of local irritation phenomena affecting the vaginal mucosa in intimate contact with a small portions of the tablet or lozenge surfaces where the drug is highly concentrated. Moreover, differently from traditional semi-solids, these systems, upon activation operated by the physiological fluids, spread their content in a very narrow surface of the vaginal epithelium leading to a lowered local action.

One possible way to solve the poor release in the vaginal secretions is to formulate the drug in ovules that melt in the vaginal cavity. However, these delivery systems cannot be marketed in the climatic zones III and IV, that is in countries where the temperatures often exceeds 30° C.

An important improvement in the field of vaginal delivery is represented by the creation of bioadhesive solid dosage forms having controlled release properties. The greatest advantage of such dosage forms is their residence in the vaginal cavity for extended periods of time including day time and night time, ensuring a predefined drug release control and thereby enabling lower dosing frequencies.

Unfortunately, the poor daily production of vaginal fluid, estimated around 6 g daily, severely limits the drug diffusion phenomena from controlled release tablets manufactured according to the present state of the art.

There is therefore the need of new therapeutic vaginal delivery system based on a bioadhesive controlled release tablet to prolong the residence time inside the vaginal cavity and to reduce the dosing intervals thanks to the drug dissolution control.

Ideally, these dosage form should combine all the advantages pertinent solely to tablets and semi-solid taken singularly, i.e.: ease of manufacturing, ease of administration, bioadhesion, efficient drug release control, chemical and physical stability, avoidance of local irritation phenomena, reduced number of dosing, jelly consistency and high drug dispersion in a broad area of the vaginal cavity.

One possible way to match these needs is the manufacture of matrix tablets comprising rate controlling excipients made by hydrophilic polymers. This technology is extensively exploited in the field of the oral delivery when a precise drug release rate is needed over a predefined period of time. Moreover, matrix tablets have found a large industrial applications for economic and reliability reasons other than being extremely effective in the development of once-daily oral dosage forms.

The technology consists of a mixture preparation dispersing the drug with soluble or insoluble hydrophilic polymers plus compression adjuvants. The mixture is then granulated or directly tableted to get the final controlled release dosage form.

Drug release occurs thanks to the swelling properties of the polymers constituting the matrix that hydrates in the presence of aqueous media thus exerting the drug release control.

According to the drug solubility, the release mechanism is based on diffusion through the swollen matrix or by polymer erosion or a combination thereof.

Drug release kinetic in turn is governed by several factors i.e. drug solubility, polymer hydration rate, polymer viscosity and loading, type and amount of fillers.

However, the need of discrete quantities of aqueous media to operate the drug release control, confined the matrix tablets in the oral delivery area where large quantities of physiological secretions are normally available in the gastro-intestinal tract.

During the inter-digestive state, the gastro-intestinal tract is subjected to an intense mechanical activity otherwise known as peristaltic wave. This phenomenon, along with the presence of food, and digestive fluids, severely modifies the capability of the swollen matrix to exercise the drug release control during the gastro-intestinal transit, leading to a mechanic smashing of the tablet with immediate release of the drug (dose dumping effect).

Oral matrix tablets should posses therefore a suitable mechanical structure at the swollen state to maintain their integrity so as to ensure a time absorption profile governed by the dissolution kinetic.

Unfortunately in the specific case of the bioadhesive controlled release vaginal delivery, the small vaginal daily secretions are not sufficient to hydrate conventional matrix tablets. This means that matrix tablets not achieving the swollen state, in practice arrest or slow down the drug diffusion process. A reduced therapeutic effect is thus expected along with localised irritation phenomena affecting the vaginal mucosa that remains in an intimate contact with the tablet for a long time interval. In these conditions the low shear forces from body movements do not allow the solid-gel transition leading the tablets to reside in the vaginal cavity for long periods without exercising any drug release.

U.S. Pat. No. 6,416,779 B1 discloses medicated devices, methods and compositions for treating vaginal disorders.

Devices may be in the form of tampons, tampon—like device, rings, pessaries, cups, sponges.

Such devices comprise a pharmaceutical agent formulated as cream, lotion, foam, ointment solution or gel incorporated thereof. The devices do not dissolve, and remain in place in the vaginal cavity so as to ensure the drug release in a timely manner (2-24 h). Devices may be designed also to absorb the blood flow.

Preferred formulations incorporated in the device consists of 0.1-10% by weight of the drug, 60-90% by weight of lipophilic or hydrophilic carrier (i.e semi-synthetic glycerides of saturated fatty acids carrier or polyethylene glycol respectively), 5-25% by weight of a mucoadhesive agent (i.e. a cellulose derivative) and optionally 5-20% by weight of a sorption promoter (i.e. ethoxy diglycol)

Devices are placed into the vaginal cavity by means of an inserter tube that need to be removed.

Adhesion of the drug released from the device to the vaginal wall is ensured by the mucoadhesive agent.

Bioadhesive tablets are mentioned as another possible drug delivery device having the shape of a tampon or a suppository to ensure thy maximum contact between the vaginal wall and the tablet surface. These bioadhesive systems comprising hydroxypropylcellulose and polyacrylic acid, are capable to release drugs up to five days once they are placed in the appropriate formulation.

WO 2006/017238 concerns coated vaginal devices for the transmucosal delivery anti-migraine and/or antinausea drugs. Coating is represented by a fluid impermeable material incorporated with a composition comprising the drug and the mucoadhesive agent. The scope of the fluid impermeable coating is to prevent the absorption of the drug once released form mucoadhesive composition into the device. As a result the drug is delivered entirely to the upper vaginal wall closest to the uterus and/or to the general circulation.

Surprisingly, it has been discovered that the inclusion of a disintegrant in an hydrophilic matrix made by one or more ether of cellulose and one or more polyacrylic acid derivatives, promoted a rapid achievement of the swollen state even in presence of limited quantities of vaginal secretions, thereby resulting in a controlled release gel spread out in a large portion of the vaginal epithelium.

The presence of the disintegrant accelerates the hydration rate of the tablets leading, in presence of shear forcers originated by body movements, to a rapid solid-gel transition in turn responsible of an immediate bio-adhesion. Differently from conventional matrix tablets for oral delivery, the bioadhesive controlled release vaginal tablets are thus designed to rapidly adhere to the vaginal epithelium and loose their shape/integrity to create a bio-adhesive gel that exercises the drug release control throughout the vaginal mucosa.

These characteristics render the controlled release bioadhesive vaginal tablets of the present invention unique, since, after the activation operated by the vaginal secretions, they combine the mutually opposing advantages pertinent to solid and semi-solid dosage forms with benefits over the patient compliance associated to ease of administration and the production costs containment.

The rapid solid-gel transition is ensured by the progressive disruption of the swollen hydrophilic matrix network exercised by the disintegrant. This phenomenon, which initially takes place from the external hydrated layers of the tablet, rapidly affects also the inner dry layers which breaks apart before hydrating thus leaving an higher surface free to swell even in presence of reduced quantity of aqueous media.

More in depth, the fast solid—gel transition is obtained thanks to the higher hydration rate of the disintegrant in comparison with that showed by the other constituents of the hydrophilic matrix namely, the ether/s of cellulose and the polyacrylic acid copolymer/s.

Such a higher hydration rate of the disintegrant is responsible of the progressive exfoliation of the dry layers of the tablets creating new surfaces that, fastening the swelling of the polymers constituting the matrix, promote the rapid formation of a jelly state shortening the time to adhere to the vaginal epithelium.

The vaginal tablets object of this invention are thus capable to ensure a quick onset of action and a prolonged therapeutic effect in an environment such as the vaginal cavity where only limited quantities of liquid secretions are available. Release mechanism is based on drug diffusion through the swollen polymers and progressive erosion/dissolution of the gel matrix.

The main advantages over the existing solid and semi-solid presentations could be summarized as follows:
low production costs, avoidance of aqueous or organic solvents, ease of self administration with no need to use applicators, gel like consistency at the activated state, avoidance of local irritation phenomena, rapid bio-adhesion, prolonged residence time associated with a controlled drug delivery, extended dosing interval, improved chemical and physical stability.

The manufacturing process of the vaginal bioadhesive controlled release matrix tablets consists of the preparation of a matrix mixture (i) comprising the following pharmaceutically acceptable excipients:
one or more ether of cellulose, one or more disintegrant, one or more polyacrylic acid copolymer.

The matrix (i) is then admixed with a mixture (ii) made by one or more drugs and functional excipients such as fillers, buffering agents, surfactants, binders, glidants, antioxidants, chelating agents, lubricants. A final mixture (iii) is thus obtained.

The final mixture (iii) is then granulated or directly compressed to obtain the final bioadhesive controlled release vaginal tablets. Advantageously the lubricant may be added to the final mixture (iii) as the last component before compression.

Common granulation processes can be used to improve the rheological and compressibility properties of the matrix (i), the drug-excipients mixture (ii), or the final mixture (iii).

The bioadhesive properties are ensured by polyacrylic acid based polymers known as Carbomers. A number of different Carbomer grades commercially available may be used. They vary in their molecular weight, degree of crosslinking structure or residual components. Among the polyacrylic acid polymers, polycarbophil, a polyacrylic acid cross-linked with divinylglycol, is preferred. This water insoluble polymer has an apparent pKa of approximately 4.5 and picks up 60-100 times its weight in water.

An exhaustive description of these polyacrylic polymers can be found on the Handbook of Pharmaceutical Excipients, fourth ed. edited by R. C. Rowe et al, Pharmaceutical Press and American Pharmaceutical Association 2003.

Controlled release properties are ensured by cellulose ethers such as hydroxypropylmethylcellulose, hydroxylpropylcellulose, hydroxyethylcellulose, methylcellulose, ethylcellulose, cellulose acetate, their derivatives and mixtures thereof. These ethers are commercialized in a number of different grades with different apparent viscosities and degree of substitution.

Preferably the cellulose ether has an apparent viscosity varying in the range of 15 cP to 100,000 cP (2% aqueous solution, 20° C.). The preferred ethers of cellulose are hydroxypropylmethylcellulose, hydroxypropylcellulose and methylcellulose.

Disintegrating agents suitable to be used in the present invention can be chosen from different classes, or mixtures thereof, here below summarized.

Modified celluloses such as cross-linked sodium carboxymethylcellulose, cross-linked polyvinylpyrrolidone such as crospovidone, natural starches such as maize starch, potato starch, directly compressible starches such as starch 1500, modified starches such as carboxymethylstarches and sodium starch glycolate, starch derivatives such as amylose, alginic acid and sodium alginate, microcrystallinbe cellulose.

Cross-linked sodium carboxymethylcellulose and crospovidone are the disintegrant preferred.

In a first preferred group, the hydrophilic matrix composition (i) consists of ether/s of cellulose 30-90% w/w; polyacrylic acid derivative/s 0.5-40%, disintegrant/s 2-50% whereas the matrix composition (i) and the drug (s) represent respectively about 5-60% and about 2-70% by weight of the tablet.

In a further preferred group, the hydrophilic matrix composition (i) consists of ether/s of cellulose 40-80% w/w; polyacrylic acid derivative/s 2-40% (preferably 2-30%, even more preferably 1-20%), disintegrant/s 5-40% whereas the matrix composition (i) and the drug (s) represent respectively about 20-40% and about 5-50% by weight of the tablet.

The controlled release properties of the vaginal tablets may be modified by the presence in the dosage form of soluble and insoluble fillers and by their weight ratio thereof.

The insoluble excipients can be selected from the group of microcrystalline cellulose, calcium phosphate tribasic, dibasic calcium phosphate, calcium sulphate and dicalcium phosphate. Dicalcium phosphate either anhydrous or hydrated is preferred.

The soluble excipients can be selected from the group of lactose, sorbitol, xylitol, mannitol, amylose, dextrose, fumaric acid, citric acid, tartaric acid, lactic acid, malic acid, ascorbic acid, succinic acid, polyethylene glycols of various molecular weight, soluble hydroxyalkylcelluloses, polyvinylpyrrolidones, gelatins, sodium carbonate, sodium bicarbonate.

To counterbalance the broad pH variations of the vaginal secretions of both pre and post menopausal women, advantageously the dosage forms may contain also one or more buffering agents to ensure a more reproducible drug release profile.

Among the variety of buffering agents, the systems calcium lactate/lactic acid, citric acid/sodium citrate and monobasic sodium phosphate either anhydrous, monohydrate or dihydrate are preferred because of their ability to give an aqueous pH in the close range of the physiological vaginal secretions of healthy pre menopausal women.

Moreover, one more advantage ensured by the buffering agent is to ensure a more reproducible in vivo viscosity of the bioadhesive polymers used (Carbomer) that, at the swollen state, is considerably reduced at pH values less than 3.0.

The bio-adhesion and the swelling extent of the hydrophilic matrix tablets of the present invention were evaluated by means of a texture analysis according to the methods described in the experimental section.

In vitro drug release test may be advantageously performed using one of the dissolution apparatus described in USP XXVIII or in EP $5^{th}$ ed.

The present invention applies to any acceptable pharmaceutical drug deliverable via vaginal route.

Advantageously, pharmaceutically acceptable surfactants might be part of the formulation to enhance the dissolution rate of actives showing a low solubility in aqueous media.

Among the variety of drugs that can be incorporated in the controlled release bioadhesive vaginal tablets object of the present invention are the antimycotics, used in the treatment of the vulvovaginal candidiasis, a common infection of *Candida Albicans* affecting approximately the 75% of women at least once during their life. The antimycotic agent may be selected from any known antimycotic agent of synthetic or natural origin. The active agent may be in the free form, i.e. as the free acid or base, or in the form of its salts. Examples include: —1-hydroxy-2-pyridone compounds and their salts, e.g. ciclopirox, rilopirox, piroctone, ciclopirox olamine and the 1-hydroxy-2-pyridone compounds disclosed in U.S. Pat. No. 4,957,730; —imidazole derivatives and their salts, e.g. Butoconazole, Clotrimazole, Econazole, Isoconazole, Ketoconazole, Miconazole, Tioconazole, Bifonazole, Fenticonazole and Oxiconazole; —polyene derivatives and their salts, e.g. Nystatin, Natamycin and Amphotericin; —allylamine derivatives and their salts, e.g. Naphtifine and Terbinafine; —triazole derivatives and their salts, e.g. Fluconazole, Itraconazole, Terconazole and Voriconazole; —morpholine derivatives and their salts, e.g. Amorolfine and morpholines disclosed in U.S. Pat. No. 5,120,530; —griseofulvin and related compounds, e.g. griseofulvin; —acidic compounds, e.g. undecylenic acid and its salts, in particular, the zinc and calcium salts of undecylenic acid; —tolnaphtate and its salts; and—flucytosine and its salts. The antimycotic agent is preferably selected from 1-hydroxy 2-pyridone compounds and their salts.

The antimycotic agent may also be selected from natural sources, in particular plant extracts. Examples of these extracts include tea tree oil (*Melaleuca attemifolia*), lavender oil (*Lavandula officinalis* chaix) and the leaf extract of the neem tree (*Azadirachta indica*).

The antimycotic agent may be used alone or in combination with other antimycotic agents. In particular, if the antimycotic agent is of natural origin, it is preferred to use it in combination. A preferred mixture is a combination of tea tree oil, lavender oil and the leaf extract of the neem tree.

The amount of the antimycotic agent will vary depending on its structure and its antimicrobial activity and the release rate from the tablet. In general, an effective amount of the antimycotic agent, i.e. an amount which is effective to kill the infecting microorganism, which will generally be several to several tens to hundreds of times greater than the mean inhibitory concentration (MIC), may be employed in the composition in accordance with the present invention. Thus, it is preferred that the amount of the antimycotic agent is in the range of 1 to 1000 mg, more preferably 5 to 500 mg, most preferably 10 to 250 mg of the unit dose.

Other active drugs that can be incorporated in the controlled release bioadhesive vaginal tablets object of the present invention are the antibiotics, as well as other antimicrobials to treat the bacterial vaginosis, the Trichomoniasis or other vulvovaginal infections.

The antibiotic agent may be selected from any known antibiotic. The antibiotic may be in the free form, i.e. as the free acid or base, or in the form of its salts. Examples include: —aminoglycosides and their salts, e.g. Amikacin, Apramycin, Arbekacin, Dibekacin, Gentamicin, Kanamycin, Neomycin, Netilmicin, Sisomicin, Streptomycin, Dihydrostreptomicin, Tobramycin; —tetracyclines and their salts, e.g. Chlortetracycline, Demeclocycline, Doxycycline, Lymecycline, Meclocycline, Methacycline, Minocycline, Oxytetracycline, Rolitetracycline, Tetracycline; —macrolides and their salts, e.g. Azithromycin, Cetromycin, Claritromycin, Dirithromycin, Erythromycin, Flurithromycin, Josamycin, Kitasamycin, Midecamycin, Oleandomycin, Pristinamycin, Dalfopristin, Rokitamycin, Roxithromycin, Spiramycin, Telithromycin, Tilmicosin, Troleandomycoin, Tylosin, Virginiamycin; —quinolones and their salts, e.g. Ciprofloxacin, Difloxacin, Enoxacin, Levofloxacin, Lomefloxacin, Moxifloxacin, Nalidixic Acid, Norfloxacin, Ofloxacin, Oxolinic Acid, Pefloxacin, Pipemidic Acid, Rufloxacin, Temafloxacin; —sulfonamides and their salts, alone or combined with diaminopyridines, e.g. co-trimoxazole; penicilline compounds and their salts, e.g. ampicillin, oxacillin, cloxacillin, dicloxacillin, flucloxacillin, amoxicillin, carbenicillin, bacampicillin; cephalosporins and other β-lactam antibiotics and their salts, e.g. cefalexine, cefaloridine, cefamandole, cefpodoxime, carbapenem derivatives, like imipenem, monobactams, like aztreonan; lincosamides and their salts, e.g. clindamycin and lincomycin.

The other antimicrobials may be selected from the group of antiprotozoarian antibacterials and their salts, including metronidazole, tinidazole, nifuratel; or from the group of antiseptics, including benzidamine, chlorexidine and the like.

The antibiotic agent may be used alone or in combination with other antibiotic agents, and/or with antiprotozoarian, and/or with antibacterials, and/or with antiseptics, and/or with antimycotic agents.

The amount of the antibiotic agent, and/or of the antiprotozoarian, and/or of antibacterial, and/or of antiseptics, will vary depending on its structure and its antimicrobial activity and the release rate from the tablet. In general, an effective amount of the antibiotic agent, or of the antiprotozoarian, or of antibacterial, or of antiseptics, i.e. an amount which is effective to kill the infecting microorganism, which will generally be several to several tens to hundreds of times greater than the mean inhibitory concentration (MIC), may be employed in the composition in accordance with the present invention. Thus, it is preferred that the amount of the antibiotic agent, or of the antiprotozoarian, or of antibacterial, or of antiseptics, is in the range of 1 to 1000 mg, more preferably 5 to 500 mg, most preferably 10 to 250 mg of the unit dose.

Since *Bacterial Vaginosis*, is associated with the alteration of both vaginal flora and natural pH of the vaginal cavity (that rises from values of 4-5 of typical healthy premenopausal women up to 7), the ability of the vaginal dosage form in maintaining an acidic pH on daily basis, further creates an unfavourable environment for microbial growth promoting the re-establishment of the natural physiological conditions.

The controlled release bioadhesive vaginal tablets of the present invention are therefore designed also to deliver pharmaceutical organic acids such as lactic acid, malic acid, citric acid, ascorbic acid, succinic acid, tartaric acid and mixtures thereof, alone or in association with one or more drugs.

Other active drugs that can be incorporated in the controlled release bioadhesive vaginal tablets object of the present invention are: pharmacological active peptidic or proteinic substances, including Calcitonin, Insulin, Desmopressin, Interferons, Endorphin and their derivatives or fragments; Releasing Factors and Releasing Hormones, other peptidic hormones, other hormones, including oestrogen and derivatives, as well as progesterone and derivatives of synthetic or natural origin, antiviral and other chemotherapeutic agents; antiviral agents being preferably selected from acyclovir, penciclovir and the like, podophyllotoxin and imiquimod; hormones being preferably selected from oestradiol, ethinyloestradiol, estriol, promestriene, hydroxyprogesterone, progesterone, medroxyprogesterone, dihydrogesterone, nomegestrol, noretisterone, tibolone, testosterone, prasterone, mesterolone, or any phytoestrogen Women who have chronic or recurring conditions may need to be treated with pharmaceutically active agents for extended periods of time. However, the oral uses of some drugs may be often unacceptable due to side effects, lower absorption, or to poor compliance. Moreover, the commercially available topical dosage forms such as creams, gels, foams pessaries and tablets are limited by their short residence in the vaginal cavity requiring a multiple daily dosing leading to poor patient compliance.

The bioadhesive controlled release vaginal tablets thanks to their characteristics are thus the right choice to counteract the oral side effect of most drugs by a topical delivery ensuring an extended dosing interval.

The invention is further illustrated by the following non limitative examples.

EXPERIMENTAL SECTION

Example 1 (Comparative Example)

Ciclopirox olamine 100 mg controlled release bioadhesive vaginal tablets lot P06-037 were produced according to the known state of the art.

The quali-quantitative formula is shown on table I.

TABLE I

| Ingredients | Quantity (mg/tablet) |
| --- | --- |
| 1. Ciclopirox olamine | 100.00 |
| 2. Hydroxypropylmethylcellulose 4,000 cps | 157.14 |
| 3. Polycarbophil | 52.38 |
| 4. Cellulose microcristalline | 125.71 |
| 5. Dicalcium phosphate anhydrous | 52.38 |
| 6. Mannitol | 261.90 |
| 7. Silicon dioxide | 5.24 |
| 8. Mg Stearate | 5.24 |
| Total | 760.00 |

The process consisted on the blending of the components 1 to 8 followed by direct compression with a rotary tableting machine (Officine Ronchi). Tablets weighing 760 mg with an hardness of 201 N were obtained. Ingredients no. 2 and no. 3 are the components of the hydrophilic matrix (i).

Example 2

Ciclopirox olamine 100 mg controlled release bioadhesive vaginal tablets lot P06-038 were produced according to the teaching of the present invention.

Tablets were prepared according to the method described in Example 1.

The quali-quantitative formula is shown on table II.

TABLE II

| Ingredients | Quantity (mg/tablet) |
| --- | --- |
| 1. Ciclopirox olamine | 100.0 |
| 2. Hydroxypropylmethylcellulose 4,000 cps | 139.05 |
| 3. Polycarbophil | 46.35 |
| 4. Na Carboxymethylcellulose XL | 76.00 |
| 5. Cellulose microcristalline | 111.24 |
| 6. Dicalcium phosphate anhydrous | 46.35 |
| 7. Mannitol | 231.75 |
| 8. Silicon dioxide | 4.63 |
| 9. Mg Stearate | 4.63 |
| Total | 760.00 |

Ingredients no. 2, 3 and 4 are the components of the hydrophilic matrix (i).

Tablets weighing 760 mg with an hardness of 248 N were obtained.

Example 3

The tablets described in Example 1 (lot P-06-037) and Example 2 (lot P-06-038) were subjected to texture analysis measurements to assess both their bioadhesive performances and their swelling extent. Tests for significant differences between means were performed by one-way ANOVA. Differences were considered significant at the P<0.05 level.

The BIOADHESIVE properties were evaluated by means of a texture analyser [1] and porcine vaginal mucosa was used as biological substrates to simulated vaginal application.

A software—controlled dynamometer (AG/MC Acquati), with a 5 daN force cell was used to measure the detachment force.

Sample Preparation
Vaginal Mucosa

Vaginal mucosae, obtained from a slaughterhouse, were deprived of the connective tissue with surgical scissors and stored at −20° C. until used. The mucosa was thawed prior to experimental use and was carefully inspected visually for any defects before fixing it on a steel plate at the bottom of the tensile apparatus by a cyanoacrylate glue. To maintain the sample hydrated, the mucosa was supported on a filter paper imbibed in deionized water and hydrated with 1 mL deionized water upon 5 min.

Testing Material

Formulation compacts of 170 mg were obtained applying a compression force of 10 tons for 30 sec by means of a hydraulic press (Glenrothes, UK), equipped with flat punches (11.28 mm diameter).

The testing material compacts were attached to the mobile steel punch by a cyanoacrylate glue.

Upon making contact between the compact and the vaginal mucosa, a constant force of 1.3N was imposed for 10 min. The mucoadhesive performance was measured in terms of detachment force required to separate the bioadhesive compact from the mucosa (maximum detachment force) upon elongation of 10 mm at the constant rate of 0.1 min/sec. The areas under the curve of the detachment force versus the elongation were also determined to represent the work or energy required to detach the two substrates. The stainless steel punch was used as negative control.

Figure 1:
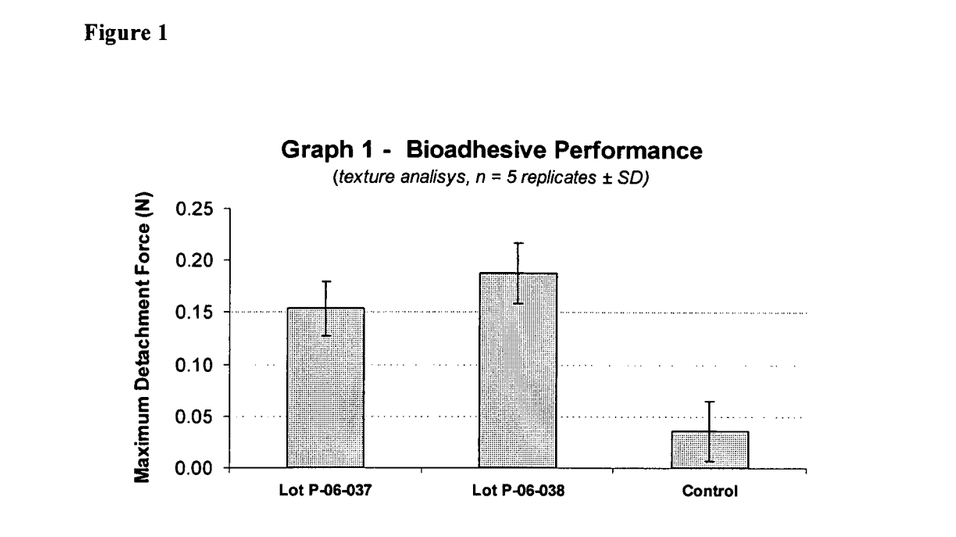
FIG. 1 shows the bioadhesive properties for formulation lots P-06-037 and P06-038.

Experimental data are summarized in FIG. 1.

Data shown in FIG. 1 indicates that both the formulation lots P-06-037 and P-06-038 possess good bioadhesive properties. In particular the highest bio-adhesion was ensured by lot P06-038 manufactured according to the teaching of the present invention. The experimental difference Vs lot P-06-037 is statistically significant (P<0.05).

The SWELLING EXTENT of the hydrophilic bioadhesive vaginal tablets were evaluated by texture analysing profiling.

Testing Material

The tablets were glued to glass plate by cyanoacrylate glue. The samples were placed in a beaker filled with 200 ml vaginal fluid stimulant (VFS) at room temperature. VFS was prepared modifying the recipe proposed by Owen and Katz [2]. The VFS was composed of the following ingredients(g): NaCl, 3.51; KOH, 1.40; $Ca(OH)_2$, 0.222; lactic acid, 2.00; acetic acid, 1.00, glycerol, 0.16; urea, 0.4; glucose, 5.0. The solution is adjusted to a pH of 4.2 using HCl.

At predetermined intervals, the swollen compacts were taken out for the textural profiling and the determination of gel layer thickness and stress-strain curves.

The movement of water penetration front and the increase in gel layer thickness were determined by a software-controlled texture analyzer (AG/MC1, Acquati, I) equipped with a 50 daN cell. The texture analyser instrument is a microprocessor controller dynamometer that registers the complete profile of stress-strain curve for the material under test. The probe is connected to a force traducer within the analyzer which measures the force of resistance encountered by the probe during the test.

During the test, the sample was positioned in the canter of the testing platform. A flat-tipped round steel probe of 5 mm in diameter was used in this study. The probe speed was 10 mm/min until the surface of the matrix was detected at 0.2 N force value (threshold value), at which point the probe penetrated the swollen matrix at a speed of 10 mm/min. Once the predetermined force was detected, the probe was automatically withdrawn at 10 mm/min.

Figure 2:
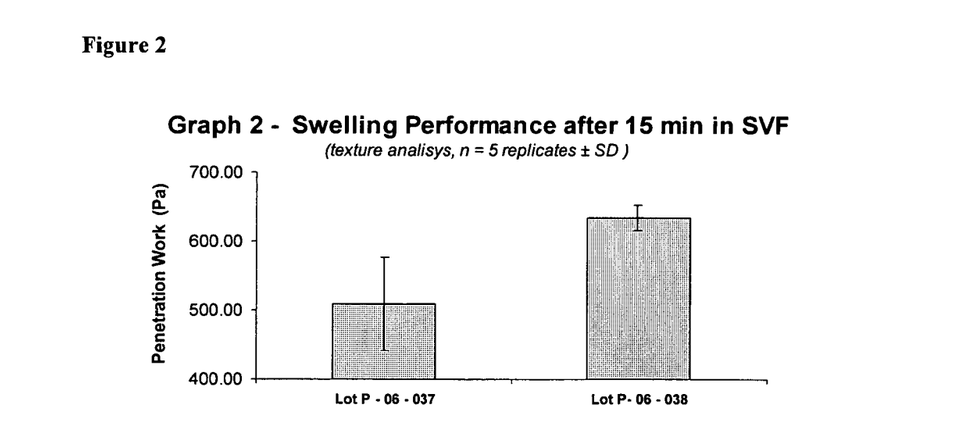
FIG. 2 shows the swelling performance for formulation lots P-06-037 and P-06-038.

Experimental data are summarized in FIG. 2.

Data shown in FIG. 2 indicate that tablets lot P-06-038 representing the object of the present invention showed, after 15 minutes of hydration in VFS, an higher swelling extent as indicated by the penetration work required. The difference Vs lot P-06-037 is statistically significant (P<0.05).

Such a higher swelling extent showed by tablets lot P-06-038 is indicative of a more rapid bio-adhesion. Moreover, the reduced standard deviation (SD), about ¼ of those originated by tablets lot P-06-037, is thought to ensure a more reliable in vivo swelling behaviour after the correct displacement of the tablets in the vaginal cavity.

By comparing graphs 1 and 2 it is clear that tablets lot P-06-038 statistically showed superior bioadhesive properties associated with a major swelling extent, the latter being in turn responsible of a more rapid adhesion to the vaginal epithelium.

Example 4

Ciclopirox 100 mg controlled release bioadhesive vaginal tablets lots P-07-022; P-07-039; P-07-049 were produced according to the teaching of the present invention.

Ciclopirox granules were obtained by a melt granulation process hereinafter detailed.

286.65 g of Ciclopirox USP, 52.50 g of PEG 6000, 10.50 g of Talc, 0.35 g of Silicon Dioxide were loaded into an high shear mixer (Rotolab Zanchetta-I). The powders were mixed for 5 minutes at 800 rpm at 20° C., then the product T was gradually increased up to 65° C. at 800 rpm in about 30 minutes.

The product was than unloaded, put on a tray, let to cool at about 40° C. and sift by 630 μm openings.

The Ciclopirox granules obtained (potency 81.9%) were than admixed with functional excipients and the mixture tableted according to the method described in Example 1

The quali-quantitative formula is shown on table III.

TABLE III

| | Ingredients | P-07-022 (mg/tablet) | P-07-039 (mg/tablet) | P-07-049 (mg/tablet) |
|---|---|---|---|---|
| 1. | Ciclopirox granules (81.9%) | 122.0 | 122.0 | 122.0 |
| 2. | Hydroxypropylmethyl-cellulose 50 cps | 139.0 | 174.0 | 208.5 |
| 3. | Carbomer | 11.6 | 11.6 | 23.2 |
| 4. | Na Carboxymethylcell-ulose XL | 38.0 | 38.0 | 38.0 |
| 5. | Cellulose microcristalline | 160.8 | 125.8 | 79.7 |
| 6. | Dicalcium phosphate anhydrous | 230.0 | 46.4 | 230.0 |
| 7. | Lactose monohydrate | 46.4 | 230.0 | 46.4 |
| 8. | Silicon dioxide | 4.6 | 4.6 | 4.6 |
| 9. | Mg Stearate | 7.6 | 7.6 | 7.6 |
| | Total | 760.0 | 760.0 | 760.0 |

Tablets weighing 760 mg with an hardness in the range of 315 N (Lot P-07-022), 314 N (lot P-07-039) and 265 N (lot P-07-049) were obtained. Ingredients no. 2, 3 and 4 are the components of the hydrophilic matrix (i).

Example 5

The tablets described in Example 4 (lots P-07-022, P-07-039; P-07-049) were subjected dissolution analysis to assess their modified release properties. The dissolution method used was: USP Dissolution Apparatus 2, 800 mL Phosphate Buffer pH 4.5, 37° C., 50 rpm, n=6, UV 297 nm. Experimental data are summarized in FIG. 3.

Figure 3:
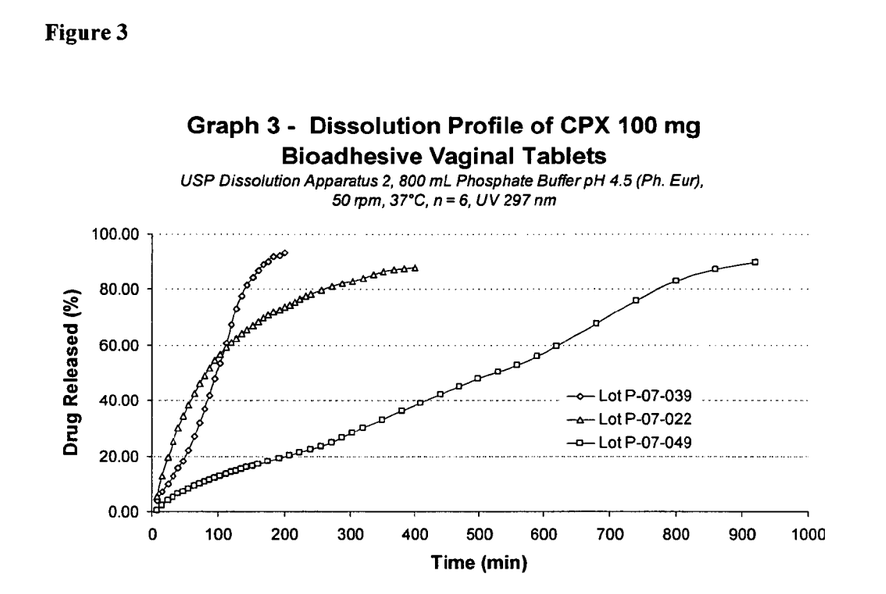
FIG. 3 shows the dissolution profiles for formulation lots P-07-022, P-07-039, and P-07-049.

All the lots show modified release properties. Their calculated T80% (time point corresponding to the 80% of drug release) resulted 141 min (lot P-07-039), 274 min (lot P-07-022), 781 min (lot P-07-049).

Example 6

The tablets described in Example 4 (lots P-07-022, P-07-039; P-07-049) were subjected to texture analysis measurements to assess their bioadhesive performances. Tests for significant differences between means were performed by one—way ANOVA. Differences were considered significant at the $P<0.05$ level.

The BIOADHESIVE properties were evaluated according to the method described in Example 3.

Figure 4:
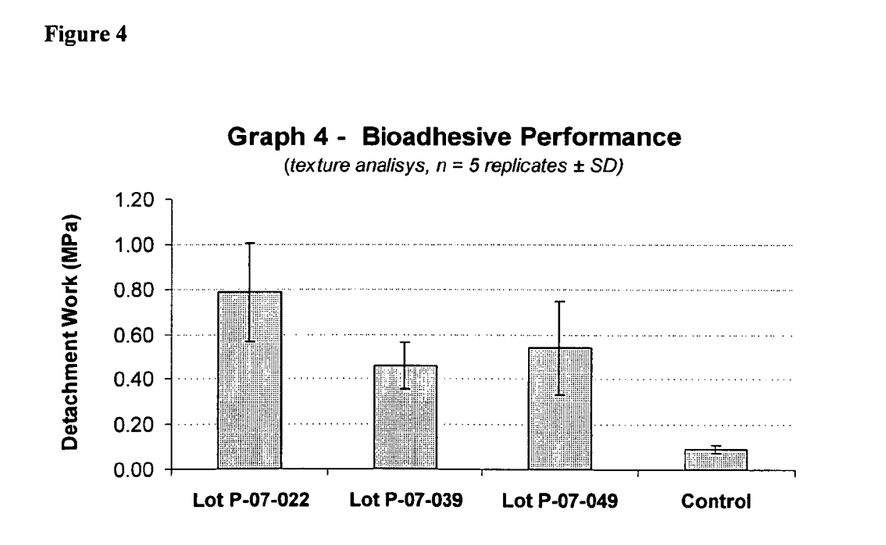
FIG. 4 shows the bioadhesive properties for formulation lots P-07-022, P-07-039, and P-07-049.

Experimental data are summarized in FIG. 4.

Data shown in FIG. 4 indicates that all the formulation lots P-07-022; P-07-039 and P-07-049, possess bioadhesive properties as clearly indicated by their detachment work Vs the control (stainless steel probe). The differences Vs the control are statistically significant ($P<0.05$).

REFERENCES

[1] Cilurzo F., Minghetti P., Selmin F., CasiraghiA., Montanari L. Polymethacryla salts as new low-swellable mucoadhesive materials, J. Control. rel., 88 (1): 43-53, 2004

[2] Owen D. H. and Katz D. F., A Vaginal Fluid Simulant. Contraception, 59: 91-95, 1999

The invention claimed is:

1. A method for the treatment of female genital disorders in a patient in need of such a treatment, wherein the female genital disorder(s) selected from the group consisting of genital hypotrophy, genital atrophy, genital loss of elasticity, vaginal dryness and/or a cervical and/or vaginal infection caused fungi, bacteria, protozoa or viruses, which method comprises administering to the patient a bioadhesive controlled release monolithic tablet containing a hydrophilic matrix, wherein the matrix is present in an amount of 20-40% with respect to the weight of the tablet, said hydrophilic matrix comprising:
   a) at least one polyacrylic acid polymer, wherein the polyacrylic acid polymer is present in an amount of 1-20% with respect to the weight of the matrix;
   b) at least one cellulose ether, wherein the cellulose ether is present in an amount of 40-80% with respect to the weight of the matrix; and
   c) a disintegrant which is cross-linked sodium carboxymethylcellulose, wherein the disintegrant is present in an amount of 5-40% with respect to the weight of the matrix;
   and at least one pharmaceutically acceptable active principle selected from the group consisting of antimycotic, antibiotic, antiviral, antimicrobial or chemotherapeutic agents and hormones, wherein the active principle is present in an amount of 5-50% with respect to the weight of the tablet.

2. The method of claim 1, wherein the at least one polyacrylic acid polymer is polyacrylic acid cross-linked with polyalkenyl ethers of sugars or polyalcohols.

3. The method of claim 2, wherein the at least one polyacrylic acid polymer is carbomer.

4. The method of claim 1, wherein the at least one polyacrylic acid polymer is a polyacrylic acid cross-linked with divinylglycol.

5. The method of claim 4, wherein the at least one polyacrylic acid polymer is polycarbophil.

6. The method of claim 1, wherein the at least one cellulose ether is selected from hydroxyalkylcellulose, alkylcellulose, carboxymethylcellulose and salts thereof.

7. The method of claim 1, wherein the at least one cellulose ether is a hydroxyalkylcellulose selected from the group consisting of hydroxypropylmethylcellulose, hydroxylpropylcellulose and hydroxyethylcellulose and/or an alkylcellulose selected from methylcellulose and ethylcellulose.

8. The method of claim 1, wherein the tablet further comprises pharmaceutically acceptable fillers, excipients and/or adjuvants.

9. The method of claim 1, wherein the antimycotic agent is selected from the group consisting of hydroxy-2-pyridone compounds, butoconazole, clotrimazole, econazole, isoconazole, ketoconazole, miconazole, tioconazole, bifonazole, fenticonazole, oxiconazole, nystatin, natamycin, amphotericin, naphtifine, terbinafine, fluconazole, itraconazole, terconazole, voriconazole, amorolfine, griseofulvin compounds, undecylenic acid, tolnaphtate, flucytosine and salts thereof.

10. The method of claim 1, wherein the antimycotic agent is ciclopirox or a salt thereof.

11. The method of claim 1, wherein the antibiotic or other antimicrobial agent is selected from the group consisting of aminoglycosides, tetracyclines, macrolides, quinolones, sulfonamides alone or combined with diaminopyridines, penicilline compounds, cephalosporins and other β-lactam antibiotics, lincosamides, antiprotozoarians, antibacterials antiseptics and salts thereof.

12. The method of claim 1, wherein the antibiotic is selected from the group consisting of nifuratel, metronidazole, tinidazole and clindamycin.

13. The method according to claim 1, wherein the antiviral agent is selected from the group consisting of idoxuridine, acyclovir, penciclovir, podophyllotoxin and imiquimod.

14. The method of claim 1, wherein the hormone is selected from the group consisting of oestradiol, ethinyloestradiol, estriol promestriene, hydroxyprogesterone, progesterone, medroxyprogesterone, dihydrogesterone, nomegestrol, noretisterone, tibolone, testosterone, prasterone, mesterolone and any phytoestrogen.

15. The method of claim 8, wherein the excipient is selected from ascorbic acid, lactic acid and salts thereof.

16. The method of claim 1, wherein said tablet is administered in the vaginal cavity.

17. The method of claim 10, wherein the antimycotic agent is ciclopirox olamine.

\* \* \* \* \*

UNITED STATES PATENT AND TRADEMARK OFFICE
CERTIFICATE OF CORRECTION

| | | |
|---|---|---|
| PATENT NO. | : 8,865,201 B2 | Page 1 of 1 |
| APPLICATION NO. | : 12/308786 | |
| DATED | : October 21, 2014 | |
| INVENTOR(S) | : Stefano De Luigi Bruschi and Federico Mailland | |

It is certified that error appears in the above-identified patent and that said Letters Patent is hereby corrected as shown below:

Title page item (56) under Foreign Patent Documents, line 10: "WO0220170" should be --WO0224170--.

Signed and Sealed this
Twentieth Day of January, 2015

Michelle K. Lee
*Deputy Director of the United States Patent and Trademark Office*